(12) United States Patent
Motai

(10) Patent No.: US 12,053,174 B2
(45) Date of Patent: Aug. 6, 2024

(54) ENDOSCOPE SYSTEM, CURVED NEEDLE DELIVERY SYSTEM, AND CURVED NEEDLE DELIVERY METHOD

(71) Applicant: OLYMPUS CORPORATION, Hachioji (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 773 days.

(21) Appl. No.: 17/141,738

(22) Filed: Jan. 5, 2021

(65) Prior Publication Data

US 2021/0121055 A1 Apr. 29, 2021

Related U.S. Application Data

(63) Continuation of application No. PCT/JP2018/028627, filed on Jul. 31, 2018.

(51) Int. Cl.
*A61B 1/00* (2006.01)
*A61B 1/018* (2006.01)
(Continued)

(52) U.S. Cl.
CPC ........ *A61B 17/062* (2013.01); *A61B 1/00135* (2013.01); *A61B 1/018* (2013.01);
(Continued)

(58) Field of Classification Search
CPC ....... A61B 1/062; A61B 1/0013; A61B 1/018; A61B 1/005; A61B 17/062;
(Continued)

(56) References Cited

U.S. PATENT DOCUMENTS 5,993,466 A * 11/1999 Yoon .................. A61B 18/1445
606/147
2006/0282089 A1 12/2006 Stokes et al.
(Continued)

FOREIGN PATENT DOCUMENTS

| CN | 102164548 A | 8/2011 |
| JP | 2003-284722 A | 10/2003 |

(Continued)

OTHER PUBLICATIONS

Sep. 7, 2021 Office Action issued in Japanese Patent Appliation No. 2020-533933.
(Continued)

*Primary Examiner* — Timothy J Neal
*Assistant Examiner* — James Edward Boice
(74) *Attorney, Agent, or Firm* — Oliff PLC

(57) ABSTRACT

An endoscope system has an overtube having a proximal end and a distal end, and a main lumen and a sub lumen; an endoscope having a channel and inserted into the main lumen; a flexible shaft being advanceable and retractable in the sub lumen; a curved needle having a proximal end and a distal end; and a needle holder configured at a distal end of the shaft to hold the curved needle, wherein the held curved needle is movable to a first position protruding from a distal end opening of the sub lumen, and due to a rotation around the longitudinal axis, part of the curved needle held by the needle holder is movable from the first position in front of the distal end opening of the sub lumen to a second position in front of the channel of the endoscope inserted into the main lumen.

9 Claims, 6 Drawing Sheets

(51) Int. Cl.
  *A61B 17/062* (2006.01)
  *A61B 1/005* (2006.01)
  *A61B 17/00* (2006.01)
  *A61B 17/06* (2006.01)
(52) U.S. Cl.
  CPC ..... *A61B 1/005* (2013.01); *A61B 2017/00296* (2013.01); *A61B 2017/0608* (2013.01)
(58) Field of Classification Search
  CPC ............ A61B 17/0469; A61B 17/0483; A61B 17/0625; A61B 17/282; A61B 17/0482; A61B 17/29; A61B 2017/00296; A61B 2017/0608; A61B 2017/3415; A61B 2017/0464; A61B 2017/0609; A61B 2017/06057; A61B 2017/2933; A61B 2017/0472; A61B 2017/00243; A61B 2017/00349; A61B 2017/00783
  USPC ....................................................... 600/104
  See application file for complete search history.

(56) References Cited

U.S. PATENT DOCUMENTS

| | | |
|---|---|---|
| 2007/0038022 A1 | 2/2007 | Nakao |
| 2011/0172706 A1 | 7/2011 | Kappel et al. |
| 2014/0187858 A1* | 7/2014 | Adams ............. A61B 17/12186 604/506 |
| 2017/0095139 A1* | 4/2017 | Yanagihara ........ A61B 17/3415 |
| 2017/0265723 A1* | 9/2017 | Yamaya ............. A61B 1/00096 |
| 2017/0304099 A1* | 10/2017 | Keren .................. A61B 17/072 |

FOREIGN PATENT DOCUMENTS

| | | |
|---|---|---|
| JP | 2006-346458 A | 12/2006 |
| JP | 2011-505920 A | 3/2011 |
| JP | 2013-223751 A | 10/2013 |
| WO | 2008-070556 A1 | 6/2008 |
| WO | 2009-073870 A1 | 6/2009 |

OTHER PUBLICATIONS

Nov. 6, 2018 Search Report issued in International Application No. PCT/JP2018/028627.

Nov. 23, 2023 Office Action issued in Chinese Patent Application No. 201880096069.5.

* cited by examiner

ENDOSCOPE SYSTEM, CURVED NEEDLE DELIVERY SYSTEM, AND CURVED NEEDLE DELIVERY METHOD

This application is a continuation application based on a PCT International Application No. PCT/JP2018/028627, filed on Jul. 31, 2018. The content of the PCT International Application is incorporated herein by reference.

TECHNICAL FIELD

The present invention relates to an endoscope system having an overtube, a curved delivery system, and a curved needle delivery method.

BACKGROUND ART

Nowadays, various treatment by introducing a flexible endoscope into gastrointestinal tract are performed. It is considered to use the flexible endoscope to perform surgical procedures more broadly, and the surgical procedures performed together with ligature procedures are also considered.

In Japanese Unexamined Patent Application, First Publication No. 2003-284722, an overtube having a curved needle disposed inside is disclosed.

In the overtube disclosed in Japanese Unexamined Patent Application, First Publication No. 2003-284722, the curved needle is connected with the overtube such that a ligature performed at a position away from the overtube is restricted. Since the ligature is performed by rotationally moving the curved needle connected with the overtube, possible aspects of the ligature are limited.

A method of grasping the curved needle using a needle grasper inserted through the endoscope and then introducing the curved needle into the body is known. In a situation in which the gastrointestinal tract is strongly curved in the body, it is possible that the curved needle interferes with an internal surface of the overtube so as to restrict the introduction of the curved needle.

SUMMARY

According to a first aspect of the present disclosure, an endoscope system includes an overtube having a proximal end and a distal end, and a main lumen and a sub lumen extending from the proximal end to the distal end; an endoscope having a channel, the endoscope being inserted into the main lumen; a flexible shaft configured to be advanceable and retractable in the sub lumen; a curved needle having a proximal end and a distal end; and a needle holder configured at a distal end of the shaft, the needle holder being configured to hold the curved needle. The held curved needle is movable to a first position protruding from a distal end opening of the sub lumen due to operations of the shaft. Due to a rotation around the longitudinal axis of the shaft, part of the curved needle that is held by the needle holder protruding from the distal end opening of the sub lumen is movable from the first position in front of the distal end opening of the sub lumen to a second position in front of the channel of the endoscope inserted into the main lumen.

According to a second aspect of the present disclosure, in the endoscope system according to the first aspect, the sub lumen may have a curved needle accommodation portion such that at least the distal end of the curved needle is accommodatable in the curved needle accommodation portion, and the needle holder may be movable to a position due to the operations of the shaft such that the distal end of the held curved needle is accommodated in the curved needle accommodation portion.

According to a third aspect of the present disclosure, in the endoscope system according to the second aspect, the curved needle accommodation portion may be a groove from in the wall of the overtube, and the curved needle accommodation portion has an opening at the distal end of the sub lumen.

According to a fourth aspect of the present disclosure, in the endoscope system according to the third aspect, the groove may be formed in a circular shape and configured to accommodate the whole curved needle.

According to a fifth aspect of the present disclosure, in the endoscope system according to the third aspect, the sub lumen may have an internal space whose cross section is formed in a non-circular shape at a more proximal side than the curved needle accommodation portion, and when part of the needle holder is positioned in the internal space, a rotation of the needle holder may be restricted.

According to a sixth aspect of the present disclosure, a curved needle delivery method using an endoscope system, wherein the endoscope system comprises an overtube having a proximal end and a distal end; an endoscope having a channel, the endoscope being inserted into the main lumen; a flexible shaft configured to be advanceable and retractable in the sub lumen; a curved needle having a proximal end and a distal end; and a needle holder configured at a distal end of the shaft, the needle holder being configured to hold the curved needle, the curved needle delivery method includes a step A of introducing the overtube into which the endoscope is inserted and the curved needle in a state in which a distal end of the curved needle is accommodated in a wall of the overtube into gastrointestinal tract; a step B after the step A to protrude the curved needle from the overtube; a step C after the step B to move part of the curved needle to a position in front of the channel of the endoscope inserted into the overtube; a step D of inserting a needle grasper into the channel of the endoscope; a step E of protruding the needle grasper from the channel and grasping part of the curved needle that is held by the needle holder using the needle grasper; and a step F after the step E to detach the curved needle grasped by the needle grasper from the needle holder.

According to a seventh aspect of the present disclosure, in the curved needle delivery method according to the sixth aspect, the step F may include operations of relatively moving the needle holder with respect to the needle grasper along the longitudinal axis of the shaft in a state of using the needle grasper to grasp the part of the curved needle held by the needle holder outside the channel.

According to an eighth aspect of the present disclosure, in the curved needle delivery method according to the sixth aspect, the step C may include operations of rotating the needle holder holding the curved needle around the longitudinal axis of the shaft.

According to a ninth aspect of the present disclosure, a curved needle delivery system includes a shaft having flexibility; a curved needle having a distal end and a proximal end; a needle holder provided at a distal end of the shaft and configured to hold the curved needle; and an overtube having a main lumen into which a treatment device is inserted and a sub lumen where the shaft is disposed in the sub lumen to be advanceable and retractable. The needle holder is configured to move the held curved needle to a first position protruding from a distal end opening of the sub lumen due to operations of the shaft, and due to a rotation around the longitudinal axis of the shaft, move part of the curved needle that is held by the needle holder protruding from the distal end opening of the sub lumen from the first position in front of the distal end opening of the sub lumen to a second position in front of the channel of the endoscope inserted into the main lumen.

According to a tenth aspect of the present disclosure, in the curved needle delivery system according to the ninth aspect, an endoscope having a channel into which the treatment device is insertable may be inserted into the main lumen.

According to an eleventh aspect of the present disclosure, in the curved needle delivery system according to the tenth aspect, the treatment device may be a needle grasper.

DESCRIPTION OF EMBODIMENT

An exemplary embodiment of the present disclosure will be described by referring to FIG. 1 to FIG. 8.

Figure 1:
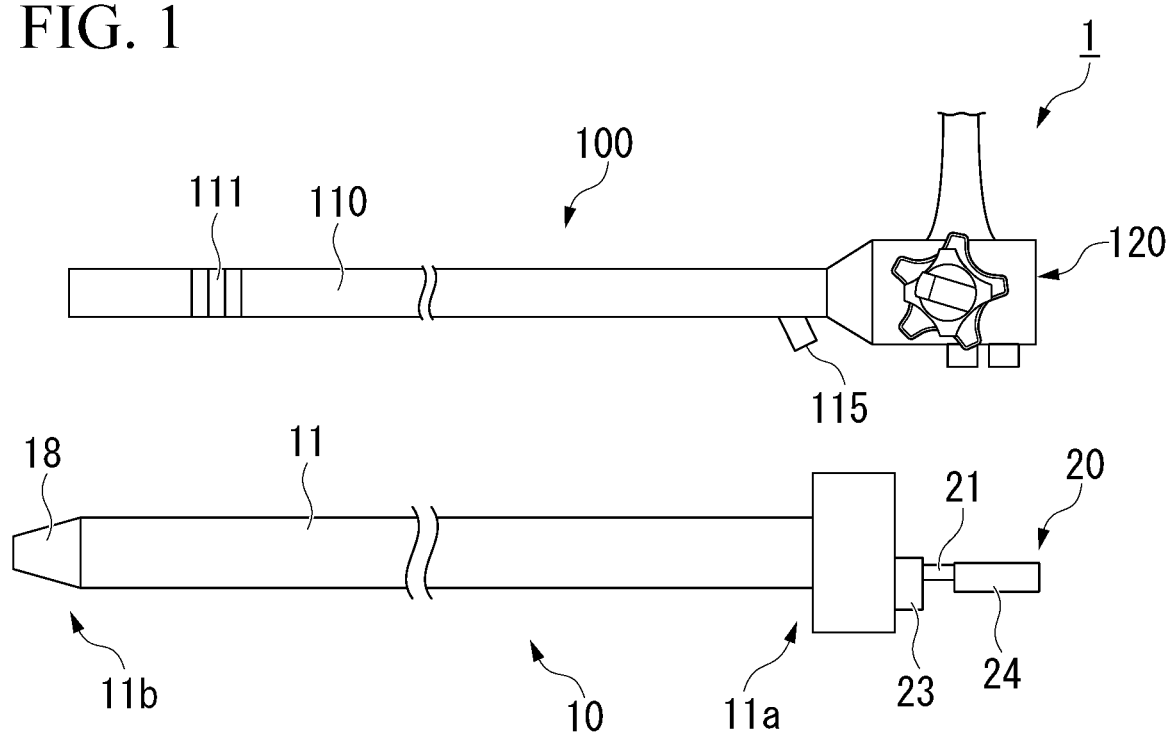
FIG. 1 is a view showing an endoscope system according to an exemplary embodiment of the present disclosure.

FIG. 1 is a view showing an endoscope system 1 according to the present embodiment. The endoscope system 1 has a flexible endoscope 100, and an overtube 10 through which the flexible endoscope 100 is inserted.

The flexible endoscope 100 has an elongated insertion portion 110 with flexibility. An operation portion 120 is disposed at a proximal end portion of the insertion portion 110. A bending portion 111 of the insertion portion 110 can be bent toward a desired direction by operating the operation portion 120. A channel for inserting a treatment device such as a needle holder, a pair of forceps, and the like is provided in the insertion portion 110. A conventional flexible endoscope can be adopted as the flexible endoscope 100 according to the present embodiment.

Figure 2:
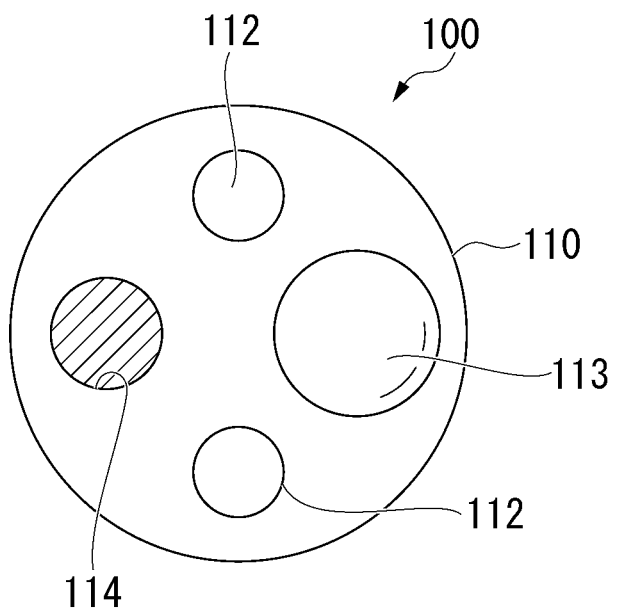
FIG. 2 is a view showing a distal end portion of a flexible endoscope according to the endoscope system.

FIG. 2 is a view showing a distal end portion of the insertion portion 110. An illumination portion 112 configured to illuminate an observation object and an observation mechanism 113 configured to acquire a video image of the observation target are disposed in the distal end portion of the insertion portion 110. The observation mechanism 113 has an optical system with lens, an imaging element and the like. A channel 114 extending in the insertion portion 110 has an opening at the distal end of the insertion portion 110. A proximal end of the channel 114 has an opening formed near the operation portion 120 as a pair of forceps opening 115 (see FIG. 1).

The overtube 10 has a tubular main body 11, and an attachment 18 and a curved needle holding device 20 which are attached to the main body 11.

Figure 3:
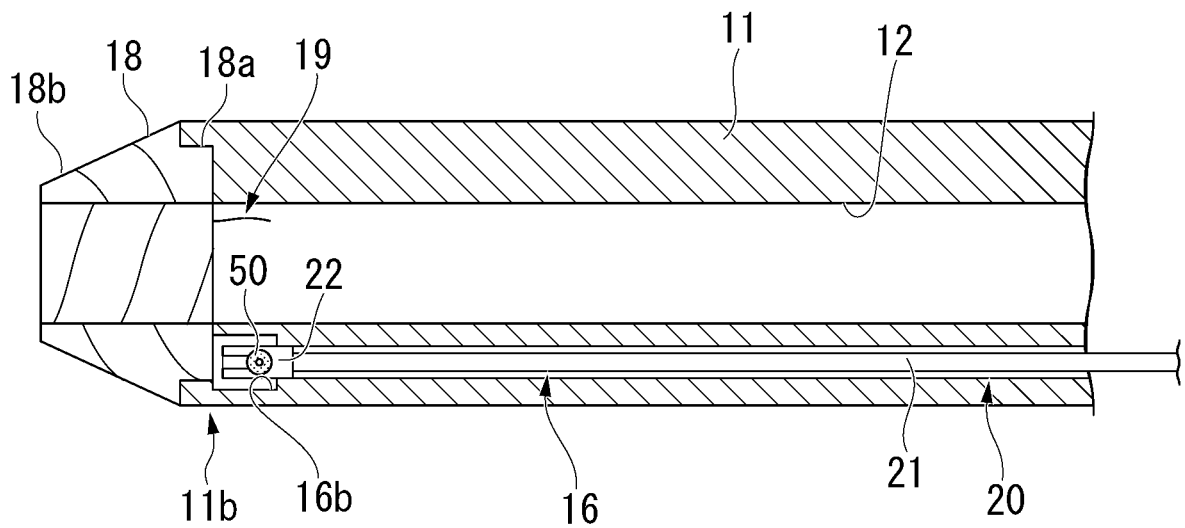
FIG. 3 is a cross-sectional view of an overtube according to the endoscope system.

FIG. 3 is a cross-sectional view of the distal end side of the overtube 10. The main body 11 is has an elongated shape and flexibility. The main body 11 has a main lumen 12 through which the insertion portion 110 of the flexible endoscope 100 is inserted, and a sub lumen 16 extending along an internal wall of the main body 11. The main lumen 12 and the sub lumen 16 extend from a proximal end 11a (see FIG. 1) toward a distal end 11b of the main body 11.

Figure 4:
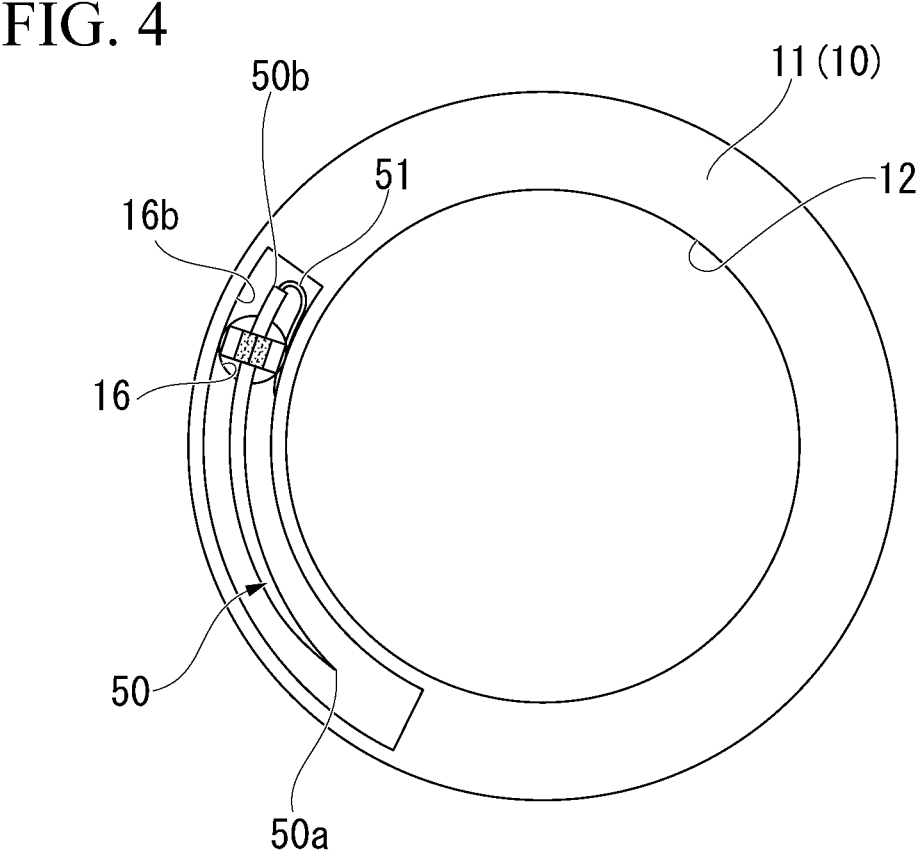
FIG. 4 is a view showing a main body of the overtube viewed from a distal end side.

The sub lumen 16 extends along a longitudinal direction of the main body 11, and the sub lumen 16 has a curved needle accommodation portion 16b extending in a circumferential direction of the main body 11 at the distal end portion of the sub lumen 16. FIG. 4 is a view showing the main body 11 viewing from the distal end 11b side in a state in which the attachment 18 is not attached to the main body 11. As shown in FIG. 4, the curved needle accommodation portion 16b is a groove having a substantial circular shape, the curved needle accommodation portion 16b opens at the distal end of the main body 11, and the curved needle accommodation portion 16b connects with the distal end of the sub lumen 16 so as to be communicated with the sub lumen 16. In other words, the curved needle accommodation portion 16b is a groove formed on the wall of the overtube 10, and opens at the distal end of the sub lumen 16.

The attachment 18 is a tubular member attached to the distal end of the main body 11, and the attachment 18 is configured to improve insertion capability of the overtube 10. The attachment 18 is formed from a flexible member, and as shown in FIG. 3, the attachment 18 has a proximal end portion 18a fitting to the main body 11, and a distal end portion 18b having a tapered shape. A thread 19 is attached to the proximal end portion 18a and extends along the internal cavity of the overtube 10.

The attachment 18 is formed by spirally winding a strip-shaped member so as to be presented in a tubular shape. Accordingly, the attachment 18 can be recovered outside the body by transforming the strip shape due to the operation described below.

As shown in FIG. 3, the curved needle holding device 20 has an elongated shaft 21 and a needle holder 22 attached to a distal end of the shaft 21.

The shaft 21 has flexibility and rotation transmissibility so as to be able to transmit a rotation around the longitudinal axis at the proximal end side to the distal end side. A coil wire formed by metal strands is considered to be a specific example of the shaft 21.

Figure 5:
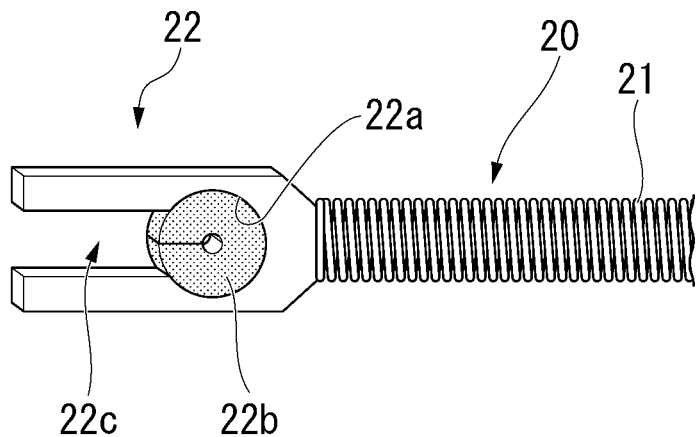
FIG. 5 is an enlarged view showing a distal end portion of a needle holding device according to the overtube.

FIG. 5 is an enlarged view showing the distal end portion of the curved needle holding device 20.

As shown in FIG. 5, the needle holder 22 according to the present embodiment is a plate-shaped member having a penetration hole 22a. The needle holder 22 only has to be able to be accommodated in the sub lumen 16, and the needle holder 22 may have other shape such as a rod shape and the like. An elastic member 22b such as a rubber, an elastomer and the like is disposed in the penetration hole 22a. A slit 22c extends from the penetration hole 22a to reach the distal end of the needle holder 22. A width of the slit 22c is larger than a diameter of the held curved needle 50 (see FIG. 4).

As shown in FIG. 4, the curved needle 50 is a needle in a substantial circular shape, and the curved needle 50 has a sharp distal end 50a and a proximal end 50b connected with a suture thread 51. The curved needle 50 is inserted through the penetration hole 22a to cause an elastic deformation of the elastic member 22b. In other words, the curved needle 50 is supported by the needle holder 22 due to an elastic restoring force of the elastic member 22b. The curved needle 50 is accommodated in the curved needle accommodation portion 16b in a state of being supported by the needle holder 22, i.e. a first state. The suture thread 51 may be accommodated in any portion of the sub lumen 16.

As shown in FIG. 3, the shaft 21 passes through the sub lumen 16. As shown in FIG. 1, a handle 24 and a stopper 23 are attached to the proximal end portion of the shaft 21 protruding from the proximal end side of the main body 11. A user can move (advance and retract) the curved needle holding device 20 along the longitudinal direction of the sub lumen 16 in the sub lumen 16 and rotate the curved needle holding device 20 around the longitudinal axis by grasping the handle 24 to operate the shaft 21.

The stopper 23 is configured to restrict a maximum advancement amount of the curved needle holding device 20 by interfering with the main body 11. A fixation position of the stopper 23 can move along the longitudinal direction of the shaft 21. The maximum advancement amount of the curved needle holding device 20 can be adjusted by changing the fixation position of the stopper 23. In a state before use, the stopper 23 is in contact with the main body 11. Accordingly, in the state before use, the shaft 21 cannot advance with respect to the main body 11.

As shown in FIG. 3, the attachment 18 attached to the main body 11 covers the distal end opening of the sub lumen 16. In other words, in a state in which the attachment 18 is attached, the curved needle 50 does not protrude into the main lumen 12 or outside the main body 11.

Operations of using the endoscope system 1 having the above-described configuration will be described.

A surgeon inserts the insertion portion 110 of the flexible endoscope 100 into the main lumen 12 from the proximal end 11a side of the overtube 10.

The surgeon inserts the overtube 10 and the flexible endoscope 100 into the gastrointestinal tract, and the surgeon moves the distal end of the overtube 10 to the vicinity of a treatment target site while using the flexible endoscope 100 to observe the inside of the body (Step A).

By performing Step A, the curved needle 50 and the suture thread 51 accommodated in the overtube 10 are also introduced in to the gastrointestinal tract of the patient.

The surgeon protrudes the flexible endoscope 100 from the overtube 10 and uses various treatment devices protruding from the channel 114 to perform treatment on the target site. The treatment devices may be inserted into the channel 114 after the overtube reaches the vicinity of the treatment target site, and the treatment devices may be inserted in advance at the time of inserting the flexible endoscope 100 into the overtube 10.

When the treatment with respect to the target site proceeds to a stage of performing the ligature, the surgeon slightly retracts the flexible endoscope 100 with respect to the overtube 10 and specifies a position of the proximal end portion 18a of the attachment 18. The surgeon grasps the thread 19 extending from the proximal end portion 18a by a pair of forceps protruding from the cannel 114 and removes the flexible endoscope 100 from the overtube 10. The proximal end portion 18a is pulled to cause the attachment 18 to be deformed into a strip shape such that the attachment 18 is decoupled from the distal end 11b of the main body 11 and recovered outside the body.

Since the attachment 18 is decoupled from the main body 11, the distal end opening of the sub lumen 16 formed in the main body 11 is exposed.

The surgeon inserts the flexible endoscope 100 into the overtube 10 again and moves the distal end of the flexible endoscope 100 to the vicinity of the distal end 11b of the main body 11. The surgeon moves the stopper 23 of the curved needle holding device 20 to a position closer to the handle 24 and pushes the handle 24. Due to operations of pushing the handle 24, the curved needle holding device 20 advances with respect to the main body 11 such that the needle holder 22 moves to make the curved needle 50 supported by the needle holder 22 to protrude from the sub lumen 16 (second state, Step B).

Immediately after Step B, the curved needle 50 only advances in the longitudinal direction of the shaft 21 such that in a front view of the main body 11, the curved needle 50 and the wall of the main body 11 substantially overlap each other. General treatment devices used together with the flexible endoscope 100 can only advance, retract, and rotate such that it is difficult to grasp the curved needle 50 at this position.

Figure 6:
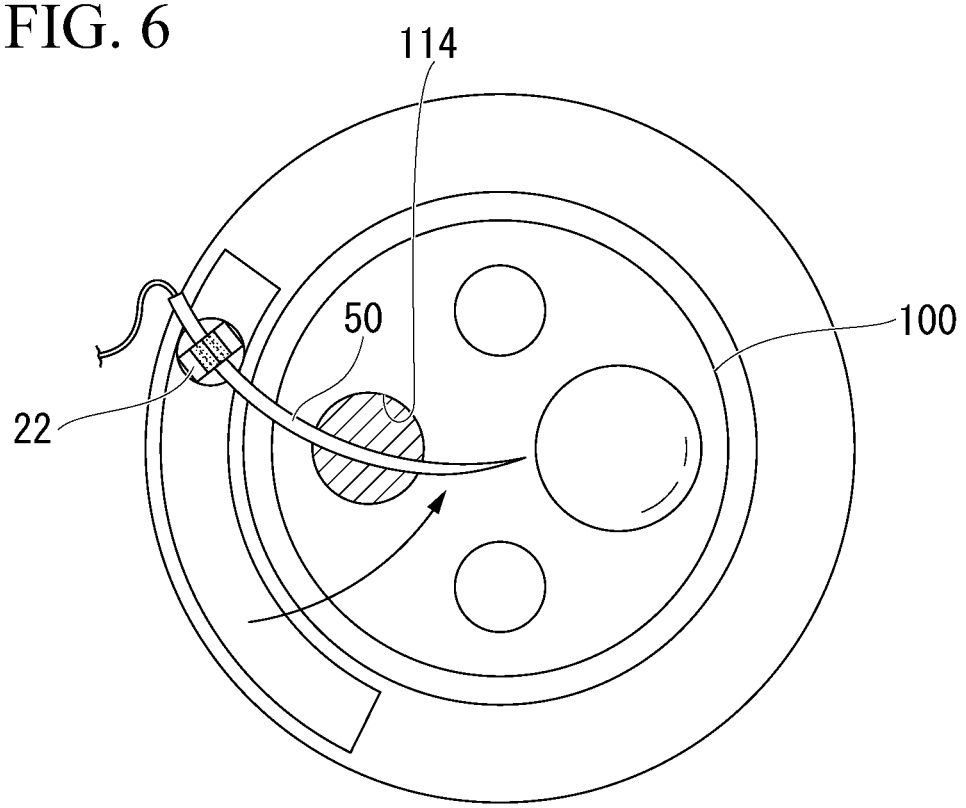
FIG. 6 is a view showing a Step C of a curved needle delivery method according to an exemplary embodiment.

When the surgeon operates the handle 24 to rotate the curved needle holding device 20 around the longitudinal axis so as to rotate the needle holder 22 and the curved needle 50, as shown in FIG. 6, it is possible to move part of the curved needle 50 to be in front of the channel 114 opening at the distal end of the flexible endoscope 100 (Step C).

Figure 7:
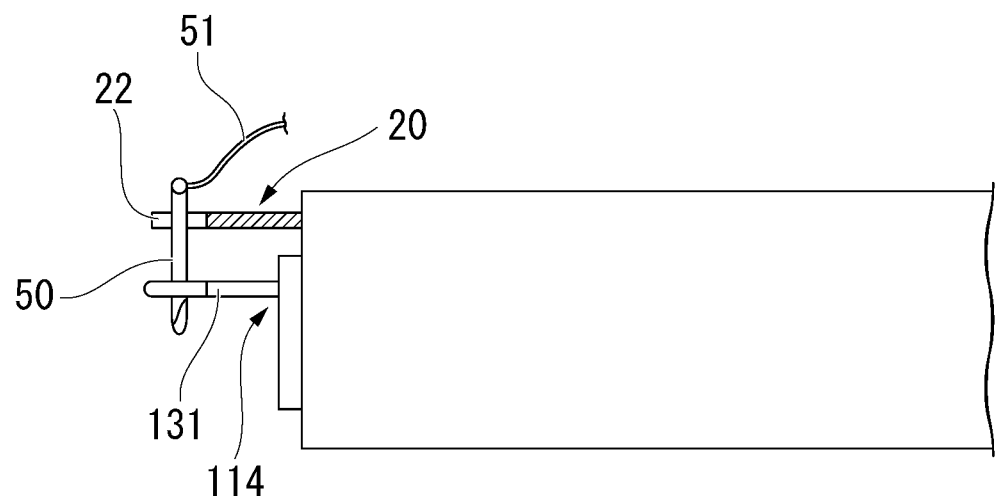
FIG. 7 is a view showing a Step E of the curved needle delivery method.

The surgeon inserts a needle grasper 131 from the forceps opening 115 (Step D), and as shown in FIG. 7, the surgeon grasps the curved needle 50 by the needle grasper 131 protruding from the channel 114 (Step E). In Step D, since the part of the curved needle moves to be in front of the channel 114, it is easy to grasp the curved needle 50 by only advancing the needle grasper 131.

Figure 8:
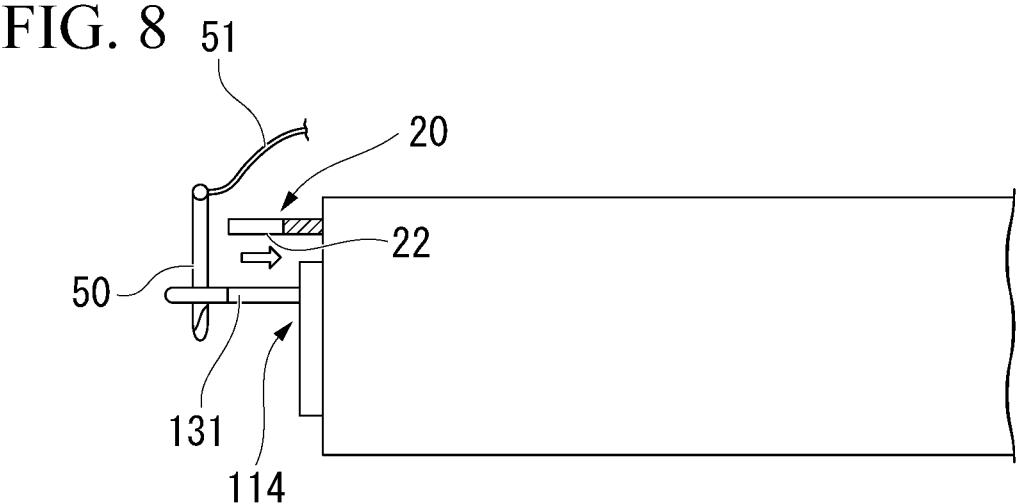
FIG. 8 is a view showing a Step F of the curved needle delivery method.

The surgeon holds the curved needle 50 by the needle grasper 131 while pulling the handle 24 to retract the curved needle holding device 20 with respect to the main body 11 and the needle grasper 131. Due to this operation, the needle holder 22 separates from the needle grasper 131 in the longitudinal direction of the shaft 21. Furthermore, the curved needle 50 grasped by the needle grasper 131 presses and separates the elastic member 22b so as to pass through the slit 22c and slips through the needle holder 22. Due to the operations, as shown in FIG. 8, the curved needle 50 is delivered from the curved needle holding device 20 to the needle grasper 131 (Step F).

The surgeon uses the needle grasper 131 holding the curved needle 50 to perform a desired ligature with respect to the target site. The flexible endoscope 100 can relatively move with respect to the overtube 10 such that it is easy to perform the ligature at a portion away from the overtube 10 and various forms of ligature can be handled.

When the ligature is finished, the surgeon cuts off the suture thread 51. The surgeon retracts the needle grasper 131 grasping the curved needle 50 and the flexible endoscope 100 with the overtube 10, and the surgeon moves the curved needle 50 grasped by the needle grasper 131 to the main lumen 12 of the main body 11. The surgeon removes the overtube 10 and the flexible endoscope 100 while keeping the state in which the curved needle 50 positions in the main lumen 12.

The curved needle delivery method according to the present embodiment has the above described Step A to Step F. According to Step A, a curved needle having a dimension which cannot be accommodated in the channel 114 of the flexible endoscope 100 can be introduced into the gastrointestinal tract without coming in contact with the gastrointestinal tract. According to Step C, the needle grasper 131 which cannot be bent itself can perform Step E.

The endoscope system 1 according to the present embodiment has the above-described overtube 10. The sub lumen 16 of the overtube 10 has the curved needle accommodation portion 16b having a substantial circular shape such that the curved needle 50 can be completely accommodated in the wall of the main body 11. As a result, the sharp distal end 50a of the curved needle 50 does not protrude to the main lumen 12 and not interfere with the flexible endoscope 100 inserted into the main lumen 12.

The curved needle holding device 20 can rotate around the longitudinal axis of the shaft 21 such that is it easy to perform Step C.

The needle holder 22 has the slit 22c extending from the penetration hole 22a until the distal end of the needle holder 22 such that it is easy to perform Step F only by retracting the curved needle holding device 20 with respect to the main body 11 while grasping the curved needle 50 by the needle grasper 131.

The curved needle holding device 20 has the stopper 23 such that it is possible to prevent the curved needle 50 from unintentionally moving outside of the sub lumen 16 after the attachment 18 is detached from the main body 11.

In a case of performing the curved needle delivery method according to the present embodiment using the endoscope system 1, in order to perform Step C and Step D smoothly, it is necessary to keep a suitable positional relationship between the channel 114 of the flexible endoscope 100 and the curved needle holding device 20.

Such an alignment can be performed using various methods such as examples shown below.

It is possible to provide a marker as a reference of the alignment at either of the overtube 10 or the flexible endoscope 100, or provide markers at both of the overtube 10 and the flexible endoscope 100.

It is possible to provide a key at either of the overtube 10 or the flexible endoscope 100, and provide a key groove at the other of the overtube 10 and the flexible endoscope 100. The key and the key groove are disposed at positions so as to make the channel 114 and the curved needle holding device 20 be in the suitable positional relationship when the key and the key groove couple with each other.

Various modifications may be made to the endoscope system and the curved needle delivery method according to the present embodiment. Hereinafter some modification will be shown as examples, however, the present disclosure is not limited thereto, other modifications may be made. At least of two modifications may be suitably combined.

Part of the curved needle accommodation portion 16b may have an opening to the main lumen 12. Furthermore, part of the curved needle 50 except for the distal end 50a may protrude from the opening.

An opening communicating with the sub lumen 16 may be formed at the external circumferential surface of the main body 11, and the end portion of the suture thread 51 connected with the curved needle 50 may be drawn out from the opening.

Instead of providing the handle 24 at the curved needle holding device 20, a configuration may be provided to grasp the shaft 21 to perform the operations.

An indicator as the reference of the position to which the stopper 23 is moved may be provided in the shaft 21. For example, it is preferable that in a case of advancing the curved needle holding device 20 is advanced until the stopper 23 positioned at the indicator interferes with the main body 11, the curved needle 50 supported by the needle holder 22 and the needle grasper 131 protruding from the channel 114 are positioned at suitable positions and shown in suitable sizes in a visual filed of the flexible endoscope 100.

Step D may be performed before Step C and Step B. Even if a frequency of only performing the ligature with respect to the target site is low, Step D may be performed before Step A.

During Step F, the curved needle holding device 20 may be rotated around the longitudinal axis of the shaft 21. In this case, a slit communicating with the penetration hole 22a only has to extend in any direction orthogonal to the longitudinal axis of the shaft and have an opening.

A second exemplary embodiment of the present disclosure will be described referring to FIG. 9 to FIG. 12. In the following description, the common configurations which have already described will be designated to the same reference sings and the reductant description will be omitted.

Figure 9:
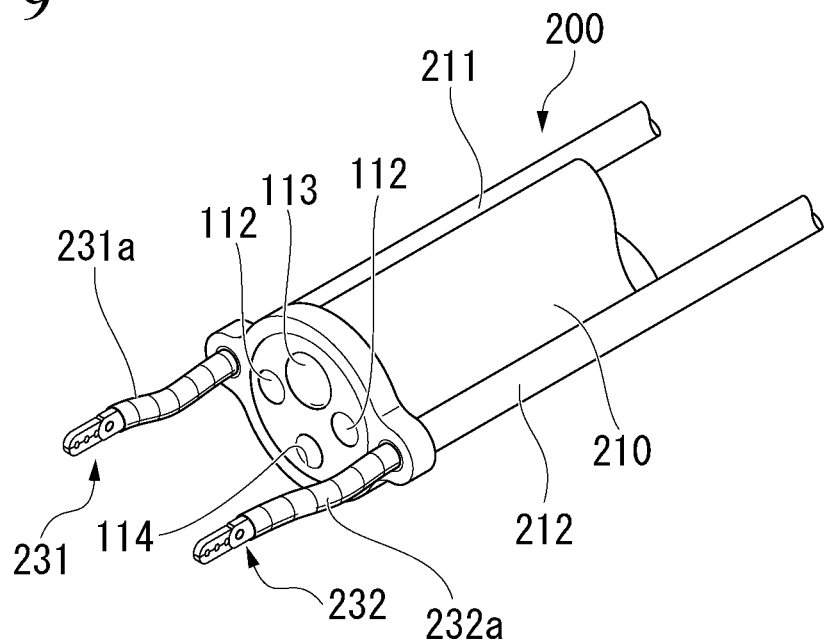
FIG. 9 is a view showing a flexible endoscope of an endoscope system according to an exemplary embodiment of the present disclosure.
Figure 10:
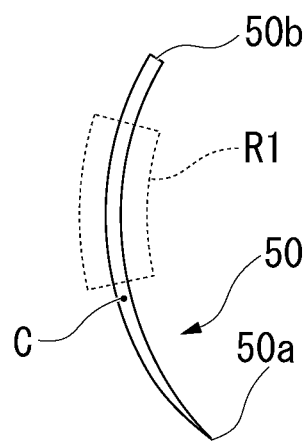
FIG. 10 is a view showing a suitable grasping range for the curved needle.

FIG. 9 shows a distal end portion of a flexible endoscope 200 according to the present embodiment. Two external channels 211, 212 are attached to an insertion portion 210 of the flexible endoscope 200. A needle grasper 231 and a needle grasper 232 are inserted through the external channel 211 and the external channel 212 respectively. The needle grasper 231 and the needle grasper 232 have a bending portion 231a and a bending portion 232a respectively. The bending portion 231a and the bending portion 232a have the same structure with the structure of the bending portion 111 of the flexible endoscope 100, and the bending portion 231a and the bending portion 232a can be bent toward desired directions by the operation of the surgeon. In other words, the needle grasper 231 and the needle grasper 232 have higher degrees of freedom than the needle grasper 131 according to the first embodiment.

Figure 11:
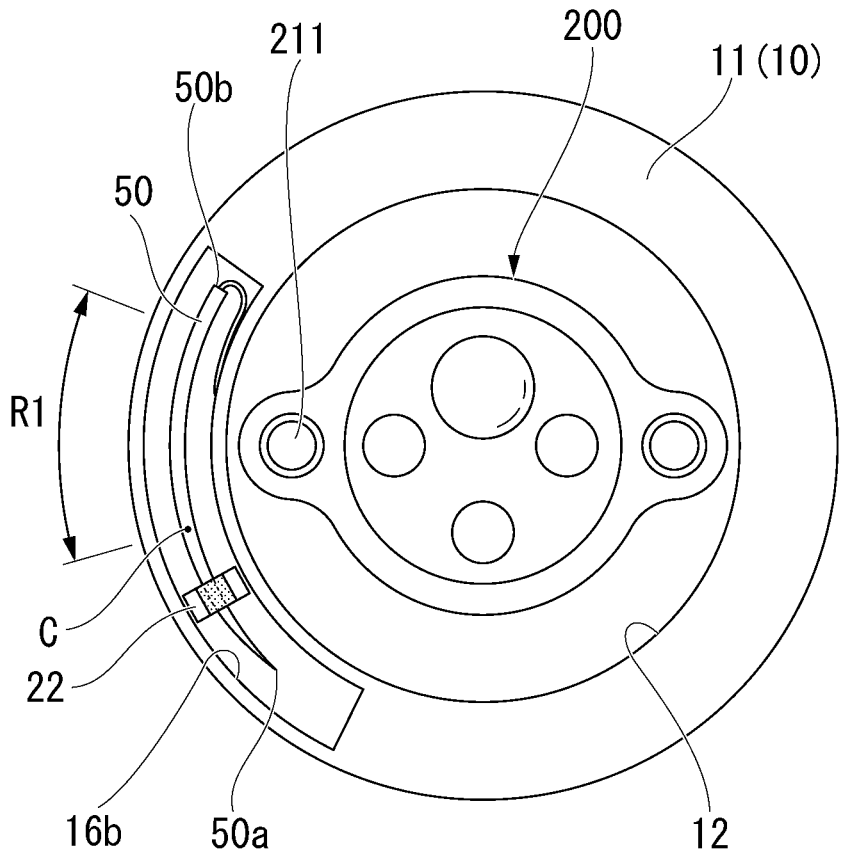
FIG. 11 is a view showing an example of a positional relationship for easily grasping the curved needle between the flexible endoscope and the overtube.

In a case of performing a curved needle delivery method by the endoscope system having the flexible endoscope 200 and the overtube 10 according to the present embodiment, in Step C, for example, when the needle holder 22 is rotated from the state shown in FIG. 11, part of the curved needle 50 moves in front of the external channel 211 such that it is easy to grasp the curved needle 50 by the needle grasper 231 protruding from the external channel 211.

In a case of performing the curved needle delivery method by the endoscope system according to the present embodiment, degrees of freedom of the needle holder 231 are high enough such that Step C may not be performed. In other words, even if the part of the curved needle 50 is not positioned in front of the external channel 211, wherein the curved needle 50 is moved outside the main body 11 in Step B, it is possible to grasp the curved needle 50 by the needle grasper 231 by operating the bending portion 231a of the needle grasper 231 to move the distal end of the needle grasper 231 toward the curved needle 50. Accordingly, the curved needle holding device according to the present embodiment may not rotatable around the longitudinal axis of the shaft.

Furthermore, in Step F, delivery of the curved needle 50 can be performed by moving the distal end portion of the needle grasper 231 holding the curved needle 50 in a direction away from the needle holder 22 so as to pull the curved needle 50 out from the penetration hole 22a.

An easiness of the ligature changes due to the position where the needle grasper grasps the curved needle 50. In the curved needle shown in FIG. 10, it is easy to perform the ligature by grasping a predetermined range R1 between an intermediate portion C and the proximal end 50b in the longitudinal direction by using the needle grasper. Hereinafter, an example of the positional relationship between the flexible endoscope 200 and the overtube 10 will be shown, wherein it is easy for the needle grasper to grasp the range R1 at the time of delivering the curved needle due to the positional relationship.

In the example of the positional relationship shown in FIG. 11, the proximal end 50a of the curved needle 50 accommodated in the curved needle accommodation portion 16b is at a position higher than the external channel 211. As a result, the range R1 is positioned at a substantially same height with the height of the external channel 211, and the range R1 is close to the external channel 211. Accordingly, a necessary movement amount of the needle grasper 231 for grasping the range R1 becomes less, and the operations in Step E become easy to perform.

Furthermore, the needle holder 22 supports the curved needle 50 between the intermediate portion C and the distal end 50a such that the needle holder 22 does not interfere with the operation of grasping the range R1 by the needle grasper 231.

Various modifications may be made to the endoscope system and the curved needle delivery method according to the present embodiment. Hereinafter some modification will be shown as examples, however, the present disclosure is not limited thereto, other modifications may be made. At least of two modifications may be suitably combined.

A number of the external channels may be one, and the number may be equal to or larger than three.

In the sub lumen 16, an internal space whose cross section is formed in a non-circular shape may be formed at a more proximal side than the curved needle accommodation portion. According to the configuration, by adjusting the advancement and retraction range of the curved needle holding device 20 to make the proximal end portion of the needle holder 22 be positioned in the non-circular-shaped internal space, in steps after Step C, the needle holder 22 cannot rotate. As a result, at the time of receiving the curved needle 50 by the needle grasper 231, it is possible to present the needle holder 22 from unintentionally rotating to obstruct the delivery of the curved needle 50.

Figure 12:
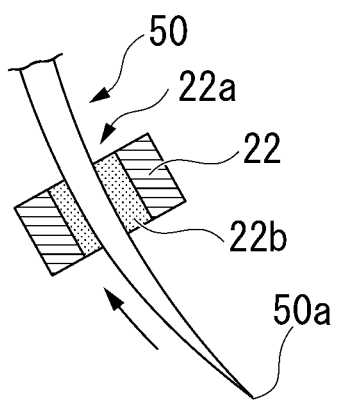
FIG. 12 is a view showing part of the curved needle and a needle holder according to a modification example.

As shown in FIG. 12, a shape of the part of the curved needle 50 passing through the penetration hole 22a may be set to have a diameter gradually becoming smaller in a direction approaching the distal end 50a. In this case, the restoring force of the elastic member 22b applies to move the curved needle 50 toward the proximal end 50b side such that the elastic member 22b may assist the operations of pulling the curved needle 50 out from the penetration hole 22a by the needle grasper 231.

Several embodiments and modification examples of the present disclosure have been described above, however, technical scope of the present disclosure is not limited to the embodiment and the application examples. Additions, omissions, substitutions and other changes in the structure are possible without departing from the spirit of the present disclosure. The present disclosure is not limited to the above-described embodiments and is limited only by the accompanying claims.

What is claimed is:

1. An endoscope system, comprising:
    an overtube having a wall, a proximal end, a distal end, and a main lumen and a sub lumen extending from the proximal end to the distal end;
    an endoscope having a channel, the endoscope being inserted into the main lumen;
    a flexible shaft configured to advance and retract in the sub lumen;
    a curved needle having a proximal end and a distal end; and
    a needle holder provided at a distal end of the shaft, the needle holder being configured to hold the curved needle,
wherein:
    the sub lumen has a curved needle accommodation portion configured to accommodate the distal end of the curved needle,
    the needle holder is configured to move to a position where the distal end of the curved needle is accommodated in the curved needle accommodation portion by operating the shaft,
    the curved needle is configured to move to a first position protruding from a distal end opening of the sub lumen by operating the shaft; and
    a portion of the curved needle that is held by the needle holder protruding from the distal end opening of the sub lumen is configured to move from the first position in front of the distal end opening of the sub lumen to a second position in front of the channel of the endoscope inserted into the main lumen by rotating the needle holder about a longitudinal axis of the shaft.

2. The endoscope system according to claim 1, wherein the curved needle accommodation portion is a groove in the wall of the overtube, and the curved needle accommodation portion has an opening at the distal end of the sub lumen.

3. The endoscope system according to claim 2, wherein the groove is formed in a circular shape and configured to accommodate the whole curved needle.

4. The endoscope system according to claim 2, wherein the sub lumen has an internal space whose cross section is formed in a non-circular shape at a more proximal side than the curved needle accommodation portion, and when part of the needle holder is positioned in the internal space, a rotation of the needle holder is restricted.

5. A curved needle delivery method using an endoscope system, wherein the endoscope system comprises:
    an overtube having a proximal end and a distal end;
    an endoscope having a channel, the endoscope being inserted into the overtube;
    a flexible shaft configured to advance and retract in the overtube;
    a curved needle having a proximal end and a distal end; and
    a needle holder provided at a distal end of the shaft, the needle holder being configured to hold the curved needle,
the curved needle delivery method comprising:
    inserting the overtube and the curved needle, in a state in which a distal end of the curved needle is accommodated in a wall of the overtube, into gastrointestinal tract;
    after inserting the overtube and the curved needle, protruding the curved needle from the overtube;

after protruding the curved needle from the overtube, moving a part of the curved needle to a position in front of the channel of the endoscope inserted into the overtube;

inserting a needle grasper into the channel of the endoscope;

protruding the needle grasper from the channel and grasping part of the curved needle that is held by the needle holder using the needle grasper; and subsequently detaching the curved needle grasped by the needle grasper from the needle holder outside the channel by moving the needle holder relative to the needle grasper along a longitudinal axis of the shaft in a state of using the needle grasper to grasp the part of the curved needle held by the needle holder outside the channel.

6. The curved needle delivery method according to claim 5, wherein moving the part of the curved needle comprises rotating the needle holder holding the curved needle around the longitudinal axis of the shaft.

7. A curved needle delivery system, comprising:
a shaft that is flexible;
a curved needle having a distal end and a proximal end;
a needle holder provided at a distal end of the shaft and configured to hold the curved needle; and
an overtube having:
a main lumen configured to accommodate a treatment device; and
a sub lumen where the shaft is disposed, the shaft being configured to advance and retract in the sub lumen,
wherein:
the sub lumen has a curved needle accommodation portion configured to accommodate the distal end of the curved needle, and
the needle holder is configured to:
move to a position where the distal end of the curved needle is accommodated in the curved needle accommodation portion by operating the shaft,
move the curved needle to a first position protruding from a distal end opening of the sub lumen by operating the shaft, and
move a part of the curved needle that is held by the needle holder protruding from the distal end opening of the sub lumen from the first position in front of the distal end opening of the sub lumen to a second position in front of the channel of the endoscope inserted into the main lumen by rotating the needle holder about a longitudinal axis of the shaft.

8. The curved needle delivery system according to claim 7, wherein:
an endoscope includes a channel, the treatment device being configured to be inserted into the channel, and
the endoscope is inserted into the main lumen.

9. The curved needle delivery system according to claim 8, wherein the treatment device is a needle grasper.

* * * * *